US008741624B2

(12) United States Patent
Skraly et al.

(10) Patent No.: US 8,741,624 B2
(45) Date of Patent: *Jun. 3, 2014

(54) PRODUCTION OF POLYHYDROXYALKANOATES FROM POLYOLS

(75) Inventors: Frank A. Skraly, Watertown, MA (US); Martha Sholl, Haverhill, MA (US)

(73) Assignee: Metabolix, Inc., Cambridge, MA (US)

( * ) Notice: Subject to any disclaimer, the term of this patent is extended or adjusted under 35 U.S.C. 154(b) by 112 days.

This patent is subject to a terminal disclaimer.

(21) Appl. No.: 12/539,079

(22) Filed: Aug. 11, 2009

(65) Prior Publication Data

US 2010/0021919 A1  Jan. 28, 2010

Related U.S. Application Data

(63) Continuation of application No. 09/909,574, filed on Jul. 20, 2001, now abandoned.

(60) Provisional application No. 60/219,995, filed on Jul. 21, 2000.

(51) Int. Cl.
*C12N 1/20* (2006.01)
*C12Q 1/68* (2006.01)
*C12N 15/00* (2006.01)
*C12N 9/02* (2006.01)
*C12N 9/04* (2006.01)
*C12N 9/00* (2006.01)
*C12P 7/42* (2006.01)
*C07H 21/04* (2006.01)

(52) U.S. Cl.
USPC ............ 435/252.33; 435/6.1; 435/320.1; 435/189; 435/190; 435/183; 435/252.3; 435/146; 536/23.2

(58) Field of Classification Search
None
See application file for complete search history.

(56) References Cited

U.S. PATENT DOCUMENTS

| 3,579,549 | A | 5/1971 | Stockmann et al. |
| 5,294,469 | A | 3/1994 | Suzuki et al. |
| 6,329,183 | B1 | 12/2001 | Skraly et al. |
| 6,576,450 | B2 | 6/2003 | Skraly et al. |

FOREIGN PATENT DOCUMENTS

| GB | 1 123 445 | 8/1968 |
| JP | 05 342903 | 12/1993 |
| JP | 06 016790 | 1/1994 |
| JP | 06 304253 | 3/1995 |
| JP | 08 226016 | 1/1997 |
| WO | WO 98/39453 | 9/1998 |
| WO | WO 99/14313 | 3/1999 |
| WO | WO 99/61624 | 12/1999 |
| WO | WO 99/64617 | 12/1999 |
| WO | WO 00/08198 | 2/2000 |

OTHER PUBLICATIONS

Stewart et al. Biotechnology and Genetic Engineering Reviews, 14:67-143.*
Baldomá & Aguilar, "Involvement of Lactaldehyde dehydrogenase in several metabolic pathways of *Escherichia coli* K12," *J. Biol. Chem.* 262:13991-96 (1987).
Boenigk, et al., "Fermentation of glycerol to 1,3-propanediol in continuos cultures of *Citrobacter freundii*," *Appl. Microbiol. Biotechnol.* 38:453-57 (1993).
Braunegg, et al., "Polyhydroxyalkanoates, biopolymers from renewable resources: physiological and engineering aspects," *J. Biotechnology* 65:127-61 (1998).
Brenda database 1.1.1.202.
Cadwell, et al., Randomization of genes by PCR mutagenesis, *PCR Methods and Applications* 2:28-33 (1992).
Dainiel, et al., "Purification of 1,3-Propanediol dehydrogenase from *Citrobacter freundii* and cloning, sequence, and overexpression of the corresponding gene in *E. coli*," *Journal of Bacteriology* 177(8):2151-2156 (1995).
Dennis, et al., "Formation of poly (3-hydroxybutyrate-co-3-hydroxyhexanoate) by PHA synthesis from *Ralstonia eutropha*," *J. Biotechnology* 64:177-86 (1998).
Doi, "Microbial Synthesis, Physical Properties, and Biodegradability of Polyhydroxyalkanoates," *Macromol. Symp.* 98:585-599 (1995).
Doi, et al., "Biosynthesis and characterization of poly(3-hydroxybutyrate-co-4-hydroxybutyrate) in *Alcaligenes eutrophus*," *Int. J. Biol. Macromol.* 12: 106 (1990).
Erickson, et al., "Enhanced biodegradation of polychlorinated biphenys after site-directed mutagenesis of a biphenyl dioxygenase gene," *Appl. Environ. Microbiol.* 59:3858-62 (1993).
ExPASY database: aldehyde dehydrogenase.
ExPASY database: diol oxidoreductase.

(Continued)

*Primary Examiner* — Yong Pak
(74) *Attorney, Agent, or Firm* — Pabst Patent Group LLP (57) ABSTRACT

Recombinant processes are provided whereby additional genes are introduced into *E. coli* which have been genetically engineered to produce PHA so that the improved strains produce PHA homopolymers and copolymers directly from diols. In preferred embodiments, PHAs containing 4-hydroxybutyrate monomers are produced directly from 1,4-butanediol; PHAs containing 5-hydroxyvalerate are produced from 1,5-pentanediol; PHAs containing 6-hydroxyhexanoate (6HH) are produced from 1,6-hexanediol; PHAs containing 3-hydroxypropionate are produced from 1,3-propanediol; PHAs containing 2-hydroxypropionate (lactate) are produced from 1,2-propanediol (propylene glycol); PHAs containing 2-hydroxyethanoate (glycolate) are produced from 1,2-ethanediol (ethylene glycol). Genes encoding these same enzyme activities can be introduced or their expression amplified in wild type PHA producers to improve the production of PHA homopolymers and copolymers directly from diol and other alcohol feedstocks. The PHA polymers are readily recovered and industrially useful as polymers or as starting materials for a range of chemical intermediates.

9 Claims, 1 Drawing Sheet

(56) References Cited

OTHER PUBLICATIONS

Forage & Foster, "Glycerol fermentation in *Klebsiella pneumoniae*: functions of the coenzyme b12-dependent glycerol and diol dehydratases," *J. Bacteriol.* 149:413-419 (1982).

Hermes, et al., "Searching sequence space by definable random mutagenesis: improving the catalytic potency of an enzyme," *Proc. Natl. Acad. Sci. USA* 87:696-700 (1990).

Hiljanen-Vaino, et al., "Biodegradable lactone copolymers. I. Characterization and mechanical behavior of □-caprolactone and lactide copolymers," *Journal of Applied Polymer Science* 59(8):1281-88 (1996).

Hiramitsu, et al., "Production of Poly(3-hydroxybutyrate-co-4-hydroxybutyrate) by *Alcaligenes latus*," *Biotechnol. Lett.* 15:461 (1993).

Ho, et al., "Site-directed mutagenesis by overlap extension using the polymerase chain reaction," *Gene* 77:51-59 (1989).

Homann, et al., "Fermentation of glycerol to 1,3-propanediol by *Klebsiella* and *Citrobacter* strains," *Appl. Microbiol. Biotechnol.* 33:121-26 (1990).

Johnson & Lin, "*Klebsiella pneumoniae* 1,3-propanediol:NAD+ oxidoreductase," *J. Bacteriol.* 169:2050-54 (1987).

Kellog, et al., "Plasmid-assisted molecular breeding: new techniques for enhanced biodegradation of persistent toxic chemicals," *Science* 214:1133-35 (1981).

Kimura, et al., "Production of Poly(3-hydroxybutyrate-co-4-hydroxybutyrate) by *Pseudomonas acidovorans*," *Biotechnol. Lett.* 14:445 (1992).

Kricheldorf, et al., "Polylactones. 1. Copolymerization of Glycolide and Epsilon-Caprolactone" *Macromolecules* 17: 2173-2181 (1984).

Kunioka, et al., "New bacterial copolyesters produced in *Alcaligenes eutrophus* from organic acids," *Polym. Commun.* 29:174 (1988).

Lee, et al., "Biosynthesis of copolyesters consisting of 3-hydroxybutyric acid and medium-chain-length 3-hydroxyalkanoic acids from 1,3-butanediol or from 3-hydroxybutryrate by *Pseudomonas* sp. A33", *Appl. Microbiol. Biotechnol.* 42:901-909 (1995).

Madison & Huisman, "Metabolic engineering of Poly(3-Hydroxyalkanoates): From DNA to Plastic," *Microbiology and Molecular Biology Reviews* 63:21-53 (1999).

Morgan, "The rapidly changing world of 1,4-butanediol," *Chemistry & Industry*, pp. 166-188 (1997).

Nakamura, et al., "Microbial synthesis and characterization of poly(3-hydroxybutyrate-*co*-4-hydroxybutyrate)," *Macromol.* 25:4237-41 (1992).

Reidhaar-Olson, et al., "Combinatorial cassette mutagenesis as a probe of the informational content of protein sequences," *Science* 241:53-57 (1988).

Saito & Doi, "Microbial synthesis and properties of poly(3-hydroxybutyrate-co-4-hydroxybutyrate) in *Comamonas acidovorans*," *Int. J. Biol. Macromol.* 16:99 (1994).

Saito, et al., "Microbial Synthesis and properties of Poly(3-hydroxybutyrate-co-4-hydroxybutyrate)," *Polym. Int.* 39:169 (1996).

Skraly, et al., "Construction and characterization of a 1,3-propanediol operon," *Appl. Environ. Microbiol.* 64:98-105 (1998).

Skraly, et al., "Polyhydroxyalkanoates produced by Recombinant *E. coli*", Poster at Engineering Foundation Conference: Metabolic Engineering, 1998.

Söhling & Gottschalk, "Molecular analysis of the anaerobic succinate degradation pathway in *Clostridium kluyveri*," *J. Bacteriol.* 178:871-880 (1996).

Spiekermann, et al, "A sensitive, viable-colony staining method using Nile red for direct screening of bacteria that accumulate polyhydroxyalkanoic acids and other lipid storage compounds," *Arch Microbiol.* 171:73-80 (1999).

Steinbuchel & Valentin, "Diversity of bacterial polyhydroxyalkanoic acids," *FEMS Microbiology Letters* 128:219-228 (1995).

Stemmer, "DNA shuffling by random fragmentation and reassembly: in vitro recombination for molecular evolution," *Proc. Natl. Acad. Sci. USA* 91:10747-51 (1994).

Stemmer, "Rapid evolution of a protein in vitro by DNA shuffling," *Nature* 370:389-91 (1994).

Streekstra, et al., "Overflow metabolism during anaerobic growth of *Klebsiella aerogenes* NCTC 418 on glycerol and dihyroxyacetone in chemostat culture," *Arch. Microbiol.* 147:268-75 (1987).

Valentin, et al., "Identification of 4-hydroxyhexanoic acid as a new constituent of biosynthetic polyhydroxyalkanoic acids from bacteria," *Appl. Microbiol. Biotechnol.* 40:710-16 (1994).

Valentin, et al., "Identification of 4-hydroxyvaleric acid as a constituent of biosynthetic polyhydroxyalkanoic acids from bacteria," *Appl. Microbial. Biotechnol.* 36:507-14 (1992).

Van Beilen, et al., "DAN sequence determination and functional characterization of the OCT-plasmid-encoded *alkJKL* genes of *Pseudomonas oleovorans*," *Mol. Microbiol.* 6: 3121-36 (1992).

Vasiliou, et al., "Eukaryotic aldehyde dehydrogenase (ALDH) genes: human polymorphisms, and recommended nomenclature based on divergent evolution and chromosomal mapping," *Pharmacogenetics* 9:421-34 (1999).

Veiga-Da-Cunha, et al., "1,3-Propanediol:NAD+ oxidoreductases of *Lactobacillus brevis* and *Lactobacillus buchneri*", *Appl Environ Microbiol.*, 58(6):2005-10 (1992).

\* cited by examiner

SEQUENCE LISTING

<160> NUMBER OF SEQ ID NOS: 8

<210> SEQ ID NO 1
<211> LENGTH: 44
<212> TYPE: DNA
<213> ORGANISM: Artificial sequence
<220> FEATURE:
<223> OTHER INFORMATION: 4hbD 5' EcoRI primer

<400> SEQUENCE: 1
ctctgaattc aaggaggaaa aaatatgaag ttattaaaat tggc      44

```
<210> SEQ ID NO 2
<211> LENGTH: 34
<212> TYPE: DNA
<213> ORGANISM: Artificial sequence
<220> FEATURE:
<223> OTHER INFORMATION: 4hbD 3' SacI primer

<400> SEQUENCE: 2
tttctctgag ctcgggatat ttaatgattg tagg                              34

<210> SEQ ID NO 3
<211> LENGTH: 47
<212> TYPE: DNA
<213> ORGANISM: E. coli
<220> FEATURE:
<221> NAME/KEY: misc_feature
<223> OTHER INFORMATION: aldH 5' Acc65I primer

<400> SEQUENCE: 3
ggtggtacct taagaggagg ttttatgaa ttttcatcac ctggctt                 47

<210> SEQ ID NO 4
<211> LENGTH: 32
<212> TYPE: DNA
<213> ORGANISM: E. coli
<220> FEATURE:
<221> NAME/KEY: misc_feature
<223> OTHER INFORMATION: aldH 3' NotI

<400> SEQUENCE: 4
ggtgcggccg ctcaggcctc caggcttatc ca                                32

<210> SEQ ID NO 5
<211> LENGTH: 47
<212> TYPE: DNA
<213> ORGANISM: Ralstonia eutropha
<220> FEATURE:
<221> NAME/KEY: misc_feature
<223> OTHER INFORMATION: gbd 5' EcoRI primer

<400> SEQUENCE: 5
cctgaattca ggaggttttt atggcgttta tctactatct gacccac                47

<210> SEQ ID NO 6
<211> LENGTH: 32
<212> TYPE: DNA
<213> ORGANISM: Ralstonia eutropha
<220> FEATURE:
<221> NAME/KEY: misc_feature
<223> OTHER INFORMATION: gbd 3' SacI primer

<400> SEQUENCE: 6
cctgagctcc tacctgcaag tgctcgccgc tc                                32

<210> SEQ ID NO 7
<211> LENGTH: 49
<212> TYPE: DNA
<213> ORGANISM: Clostridium kluyveri
<220> FEATURE:
<221> NAME/KEY: misc_feature
<223> OTHER INFORMATION: orfZ 5' AvrII primer

<400> SEQUENCE: 7
tcccctagga ttcaggaggt ttttatggag tgggaagaga tatataaag              49

<210> SEQ ID NO 8
<211> LENGTH: 38
<212> TYPE: DNA
```

```
<213> ORGANISM: Clostridium kluyveri orfZ
<220> FEATURE:
<221> NAME/KEY: misc_feature
<223> OTHER INFORMATION: orfZ 3' SalI primer

<400> SEQUENCE: 8
ccttaagtcg acaaattcta aatctcttt ttaaattc                           38
```

US 8,741,624 B2

PRODUCTION OF POLYHYDROXYALKANOATES FROM POLYOLS

CROSS REFERENCE TO RELATED APPLICATIONS

This application is a continuation of pending prior application U.S. Ser. No. 09/909,574 filed Jul. 20, 2001, entitled "*Production of Polyhydroxyalkanoates From Polyols*", by Frank A. Skraly and Martha Sholl, which claims priority to U.S. Provisional Application Ser. No. 61/219,995, filed on Jul. 21, 2000, all of which are herein incorporated in their entirety by reference.

BACKGROUND OF THE INVENTION

This invention is generally in the field of production of polyhydroxyalkanoates (PHAs) by genetic engineering of bacteria.

Synthesis of PHA polymers containing the monomer 4-hydroxybutyrate (4HB), such as poly(3-hydroxybutyrate-co-4-hydroxybutyrate) (PHB4HB) (Doi, 1995, *Macromol Symp.* 98:585-99) or 4-hydroxyvalerate and 4-hydroxyhexanoate containing PHA polyesters have been described, for example, in Valentin et al., 1992, *Appl. Microbial. Biotechnol*, 36:507-14 and Valentin et al., 1994, *Appl. Microbiol. Biotechnol.* 40:710-16. Production of PHB4HB, for example, has been accomplished by feeding glucose and 4HB or a substrate that is converted to 4-hydroxybutyrate to *Ralstonia eutropha* (Kunioka, et al., 1988, *Polym. Commun.* 29:174; Doi, et al., 1990, *Int. J. Biol. Macromol.* 12:106; Nakamura, et al., 1992, *Macromolecules* 25:423), to *Alcaligenes latus* (Hiramitsu, et al., 1993, *Biotechnol. Lett.* 15461), to *Pseudomnonas acidovorans* (Kimura, et al., 1992, *Biotechnol. Lett.* 14:445), and to *Comamonas acidovorans* (Saito & Doi, 1994, *Int. J. Biol. Macromol.* 16:18). Substrates that are converted to 4HB include 1,4-butanediol, 1,6-hexanediol, 1,8-octanediol, 1,10-decanediol, 1,12-dodecanediol and gamma-butyrolactone. The PHB4HB copolymers can be produced with a range of monomer compositions which provide a range of polymer properties. In particular, as the amount of 4HB increases above 15 wt. %, the melting temperature ($T_m$) decreases below 130° C. and the elongation to break increases above 400% (Saito, et al., 1996, *Polym. Int.* 39:169).

It would be highly advantageous, however, to develop more cost effective ways of producing PHAs containing 4HB by biological systems. For economic production of PHA, several factors are critical, including substrate costs, fermentation time, and efficiency of downstream processing. A general characteristic of the wild type PHA-producing bacteria is that their growth rate is low, they are often difficult to break open and their amenity to genetic engineering is limited. Therefore, it would be desirable to develop transgenic organisms that provide improved economics of PHA production.

The production of the copolymer PHB4HB in recombinant *E. coli* has been described (e.g., PCT WO 00/011188 by Huisman et al.; PCT WO 98/39453 by Hein et al.). A range of novel biologically produced 4HB polymers produced in recombinant *E. coli* have been described by Skraly and Peoples (e.g., PCT WO 99/61624). In these studies only the Huisman reference demonstrated the incorporation of small amounts of 4HB co-monomer from 1,4-butanediol. It would be highly advantageous to develop genetically engineered systems capable of the production of a range of 4HB copolymers and poly-4HB homopolymer using 1,4-butanediol as the source of the 4HB monomer.

It is therefore an object of the present invention to provide improved recombinant systems and methods for the production of PHAs, such as PHAs containing the 4HB monomer, using a variety of simple sugars and alcohols as substrates.

SUMMARY OF THE INVENTION

Recombinant processes are provided whereby additional genes are introduced into *E. coli* which have been genetically engineered to produce PHA so that the improved strains produce PHA homopolymers and copolymers directly from diols. In preferred embodiments, PHAs containing 4-hydroxybutyrate (4HB) monomers are produced directly from 1,4-butanediol; PHAs containing 5-hydroxyvalerate (5HV) are produced from 1,5-pentanediol; PHAs containing 6-hydroxyhexanoate (6HH) are produced from 1,6-hexanediol; PHAs containing 3-hydroxypropionate (3HP) are produced from 1,3-propanediol (also called propylene glycol); PHAs containing 2-hydroxypropionate (2HP, lactate) are produced from 1,2-propanediol (propylene glycol); PHAs containing 2-hydroxyethanoate (2HE, glycolate) are produced from 1,2-ethanediol (ethylene glycol). Genes encoding these same enzyme activities can be introduced or their expression amplified in wild type PHA producers to improve the production of PHA homopolymers and copolymers directly from diol and other alcohol feedstocks. The PHA polymers are readily recovered and industrially useful as polymers or as starting materials for a range of chemical intermediates.

DETAILED DESCRIPTION OF THE INVENTION

Processes are provided whereby additional genes are introduced into microorganisms which have been genetically engineered to produce PHA so that the improved strains produce PHA homopolymers and copolymers directly from simple alcohol and sugar substrates. These processes are based on recombinant bacteria e.g., *Escherichia coli* as a production organism and PHA biosynthetic genes from PHA-producing microbes such as *Ralstonia eutropha* or *Alcaligenes latus* although many other sources of PHA genes are now known (Madison & Huisman, 1999, *Microbiol. & Molecular Biology Reviews*, 63:21-53). Recombinant *E. coli* has many advantages over the wild type PHA producing organisms including ease of genetic manipulation, complete availability of the genome sequence, fast growth rate, flexibility of growth substrates and ready lysis.

Organisms to be Engineered

Figure 1:
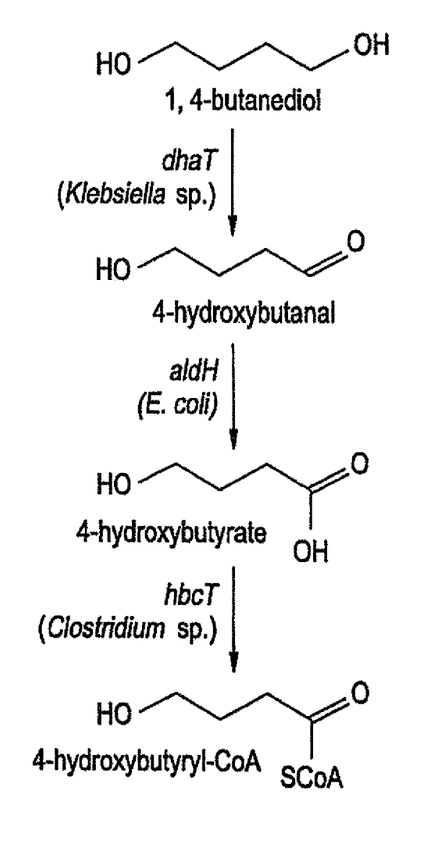
FIG. 1 illustrates the pathway from 1,4-butanediol to 4-hydroxybutyryl-CoA that is employed in one embodiment.

In one embodiment, genes for the entire pathway illustrated in FIG. 1 are introduced into the production organism. An organism that does not naturally produce PHAs, such as *Escherichia coli*, may be used. A number of recombinant *E. coli* PHB production systems have been described (Madison & Huisman, 1999, *Microbiology & Molecular Biology Reviews*, 63:21-53). The genes encoding a diol oxidoreductase and aldehyde dehydrogenase are introduced into this host. In the case of 1,4-butanediol, the diol oxidoreductase converts the substrate to 4-hydroxybutyraldehyde, which is then converted to 4-hydroxybutyrate by the aldehyde dehydrogenase. In the case of 1,3-propanediol, the diol oxidoreductase converts the substrate to 3-hydroxypropionaldehyde, which is then converted to 3-hydroxypropionate by the aldehyde dehydrogenase. Other diols may be treated in an analogous way. In some instances incorporation into PHA of a hydroxyacid that is two carbons shorter than the diol feedstock may occur. This is due to endogenous catabolism resembling that of the beta-oxidation pathway of fatty acid catabolism. For example, 4HB units, or both 4HB and 6HH units, may be produced in the polymer as a result of feeding 1,6-hexanediol. Optionally an exogenous acyl-CoA transferase or acyl-CoA synthetase may be included to facilitate activation of the hydroxyacid with coenzyme A. The activated monomer may then be incorporated into PHA by the action of an appropriate PHA synthase present in the production host. The enzyme activities provide a system for the synthesis in the production host of a polymer containing one or more monomer types, depending upon the diol feedstocks.

It is often very useful to synthesize copolymers containing monomers like those mentioned above and 3HB. In this case, the production host will also contain the β-ketothiolase and acetoacetyl-CoA reductase genes, the products of which convert acetyl-CoA to 3HB-CoA. Acetyl-CoA may be derived from the diol or from another carbon source such as a sugar. Both 3HB-CoA and hydroxyacyl-CoAs such as those mentioned above can be accepted by various PHA synthases such as the one expressed in the recombinant host, and therefore copolymers of PHB are synthesized by the recombinant host. Whatever the desired PHA composition, the diol can be fed to the cells either during growth or after a separate growth phase, either alone or in combination with at least one other feedstock, such as a sugar, and PHA is accumulated within the cells.

In another embodiment, a recombinant organism that naturally contains at least part of the pathway shown in FIG. 1 can be used. In this embodiment one or more of the activities discussed above (diol oxidoreductase, aldehyde dehydrogenase, acyl-CoA transferase or acyl-CoA synthetase, β-ketothiolase, PHA synthase, and acetoacetyl-CoA reductase) can be derived from the endogenous machinery of the host. For example, only diol oxidoreductase and aldehyde dehydrogenase might be expressed in *R. eutropha*, a natural PHA-producing organism, to augment its ability to convert 1,4-butanediol to 4HB, and the natural ability of the host may be relied upon to accomplish the rest of the necessary metabolic steps. Many natural PHA-producing organisms are well-known to those skilled in the art (Braunegg et al. 1998, *J. Biotechnology* 65: 127-61). If the host is not capable of PHA production, a PHA synthase or an entire PHB biosynthetic pathway and optionally an exogenous acyl-CoA transferase or acyl-CoA synthetase may be introduced into this organism to enable PHA production. Techniques for doing this are well known in the art (for example, Dennis et al., 1998, *J. Biotechnology* 64:177-86). Here also, the diol can be fed to the cells either during growth or after a separate growth phase, either alone or in combination with at least one other feedstock, such as a sugar, and PHA is accumulated within the cells.

The implementation of the production of PHAs with diol feedstocks is not limited to bacteria as described in the examples. The same genes may be introduced into eukaryotic cells, including but not restricted to, yeast cells and cultured plant cells.

Genes for Utilization of Substrates

Genes and techniques for developing recombinant PHA producers suitable for use as described herein are generally known to those skilled in the art (Madison & Huisman, 1999, *Microbiology and Molecular Biology Reviews*, 63:21-53; PCT WO 99/14313). Because all of the genes necessary to implement the production of PHAs from feedstocks such as diols and sugars have been cloned and are available in genetically manipulatable form, any combination of plasmid-borne and integrated genes may be used, and the implementation of this pathway is therefore not restricted to the schemes outlined herein. Many different implementations will be apparent to those skilled in the art.

1,3-Propanediol oxidoreductase (EC 1.1.1.202) is found in several species of bacteria. Often it is induced under anaerobic conditions in the presence of glycerol (Forage & Foster, 1982, *J. Bacteriol.* 149:413-419). This enzyme catalyzes the reversible formation of 3-hydroxypropionaldehyde and other hydroxyaldehydes from the corresponding diol. Physiologically the enzyme is thought to be primarily used in diol formation, when the aldehyde is needed as an electron acceptor at the expense of NADH (Johnson & Lin, *J. Bacteriol.* 169.2050-54). Organisms that contain 1,3-propanediol oxidoreductase typically are able to convert glycerol to 1,3-propanediol, though similar activities are found in other organisms. Bacterial species noted for the ability to convert glycerol to 1,3-propanediol include *Klebsiella pneumoniae* (Streekstra et al., 1987, *Arch, Microbiol.* 147:268-75), *Klebsiella oxytoca* (Homann et al., 1990, *Appl. Microbiol. Biotechnol.* 33:121-26), *Klebsiella planticola* (Id.) and *Citrobacter freundii* (Boenigk et al., 1993, *Appl. Microbiol. Biotechnol.* 38:453-57) although many other examples are generally known.

Aldehyde dehydrogenases are extremely common in biological systems. Probing the *E. coli* genome database for homology shows that this organism alone contains at least seven putative enzymes of this type. They are so numerous and varied that even attempts to classify them all are complicated (e.g. Vasiliou et al., 1999, *Pharmacogenetics* 9:421-34). A discussion of all of the types and physiological roles of these enzymes is beyond the scope of this discussion. The choice of an appropriate aldehyde dehydrogenase for use in metabolic engineering should be done after evaluation of the substrate specificity of several candidates. Enzyme assays such as that described in Baldomá & Aguilar (11987, *J. Biol. Chem.* 262:13991-6) are useful for such diagnoses.

Acyl-CoA transferases (EC 2.8.3.x) and acyl-CoA synthetases (EC 6.2.1.x) both catalyze the formation of thioesters of organic acids with coenzyme A. Acyl-CoA transferases, such as OrfZ (also called HbcT) (Söhling and Gottschalk, 1996, *J. Bacteriol* 178:871-80) transfer the CoA moiety from a donor such as acetyl-CoA to a free organic acid, such as a fatty acid. Acyl-CoA synthetases such as AlkK (van Beilen et al., 1992, *Mol. Microbiol.* 6: 3121-36) ligate free organic acid and free coenzyme A, deriving the energy for the reaction from ATP and leaving AMP and pyrophosphate as byproducts.

Improvements in the Enzymes in the Pathway

It may be advantageous to improve the specific activity or substrate specificity of the enzymes in the diol-to-PHA pathway described herein. For example, a specific diol may not be converted to PHA at an acceptable rate in a specific organism. Improvements of this nature will generally involve mutagenesis and screening; the DNA sequence(s) to be improved are subjected to one or more rounds of mutagenesis followed by an assessment of improvements made.

Mutagenesis can be implemented using any of a variety of ways knows to those skilled in the art (e.g., error-prone PCR or cassette mutagenesis, passage through bacterial mutator strains, treatment with chemical mutagens), such as those described by Cadwell et al., 1992, *PCR Methods and Applications* 2:28-33; Erickson et al., 1993, *Appl. Environ. Microbiol.* 59:3858-62; Hermes et al., 1990, *Proc. Natl. Acad. Sci. USA* 87:696-700; Ho et al., 1989, *Gene* 77:51-59; Kellog et al., 1981, *Science* 214:1133-35; Reidhaar-Olson et al., 1988, Science 241:53-57; Stemmer, 1994, *Nature* 370:389-91; and Stemmer, 1994, *Proc. Natl. Acad. Sci. USA* 91:10747-51.

Screening for an improved diol-to-PHA pathway involves culturing a population of mutants generated as described above in such a way that cells improved in some property relating to the pathway can be selected readily. One embodiment is the selection for improved growth on the diol of interest. An organism deficient in uptake or utilization of a particular diol will not grow well with that diol as the sole carbon source. A pool of mutants can be inoculated into liquid medium or onto agar plates containing the diol as sole carbon source, along with all other nutrients necessary for growth of the organism in question, and cells able to grow may be readily isolated. Another embodiment is the selection of cells able to produce polymer when cultured in the presence of the diol. If an organism is unable to convert the diol at a significant rate to a monomer precursor that can subsequently be polymerized, plating that organism on agar containing the diol as the sole carbon source (other than carbon contained in any complex supplements added, such as yeast extract) will yield cells with little or no PHA content. Culturing a pool of mutants on such a plate can identify strains that have gained the ability to convert the diol to polymerizable intermediates. These cells will appear more opaque and white than the non-PHA-producing cells. Alternatively, another carbon source such as glucose may be added if the cells to be screened cannot synthesize polymer from that carbon source. Plates can also serve to eliminate strains that cannot grow in the conditions it presents; for example, a cell that has gained via mutagenesis the ability to produce PHA from diol, but has lost an industrially important characteristic such as the ability to grow on minimal glucose medium, will not grow on plates containing diol and glucose, especially if it cannot grow on the diol as sole carbon source. Only the cells that can produce PHA from diol and can grow on minimal glucose in this case will appear as opaque colonies. PHA can be visualized within cells, especially on plates, by methods more sensitive than visual screening of untreated colonies, such as by staining with Nile red (as in, e.g., Spiekermann et al, 1999, *Arch Microbiol.* 171:73-80). Methods such as those above may be repeated for several rounds to further optimize the diol-to-PHA pathway. Methods of screening are illustrated by, but not restricted to, the aspects of the discussion above, and other useful screening procedures will be apparent to those skilled in the art.

Regulation of Expression

In any of the aforementioned embodiments, it is possible to control the composition of the polymer produced by controlling the expression of the diol oxidoreductase and aldehyde dehydrogenase or by controlling the availability of the diol. The higher the activities of diol oxidoreductase and aldehyde dehydrogenase, the more activated monomer will be derived as a result of their activities, up to the point where another factor such as substrate availability or an enzyme activity downstream of these becomes limiting. Methods for modulation of gene expression (and thus enzyme activity) in various organisms are well-known to those skilled in the art. The rate of diol feed to the cultured cells can be controlled by various techniques well-known to those skilled in fermentation and cell culture.

In the case of some microorganisms, some or all of the genes can be integrated into the host chromosome and some or all provided on a plasmid. In some cases, compatible plasmid systems can be used, for example, with several steps of the pathway encoded on one plasmid and the other steps encoded by a second plasmid. A combination of the two approaches may also be used.

Substrates

As discussed above, substrates that can be used to make PHAs in the context of the systems described herein include alcohols, preferably diols. Examples of suitable diols include 1,6-hexanediol, 1,5-pentanediol, 1,4-butanediol, 1,3-propanediol, 1,2-ethanediol, and 1,2-propanediol.

These diols are nontoxic to many microorganisms, in many cases even at high concentrations. They can be superior feedstocks for fermentation as compared to organic acids, which often become toxic at low concentrations to many microorganisms. Many diols are readily available and relatively inexpensive. For example, 1,4-butanediol had a global demand of about 1 billion pounds in 1995 and is very widely used for synthetic polymer production (Morgan, *Chemistry & Industry*, 3 Mar. 1997, pp. 166-8).

The present invention will be further understood by reference to the following non-limiting examples.

Example 1

Enzymatic Assay of *Escherichia coli* AldH

On the basis of its homology with other aldehyde dehydrogenases, the aldH gene was cloned by PCR from the *E. coli* genome. Plasmid pMS33 contains aldH under the control of the trc promoter. *E. coli* DH 5α was transformed with pMS33 or pFS14, as a negative control. Plasmid pFS14 contains the *Clostridium kluyveri* 4hbD (4HB dehydrogenase) gene, as described in Söhling and Gottschalk (1996, *J. Bacteriol.* 178: 871-80).

DH5α/pMS33 and DH5α/pFS14 were grown at 37° C. with shaking in Luria-Bertani (LB; Difco; Detroit, Mich.) broth to an optical density (600 nm) of 0.5 and subsequently induced with 1 mM isopropyl-β-D-thiogalactopyranoside (IPTG). The incubation continued for 3 hours, after which the cells were removed from the medium by centrifugation (2000 g, 10 min.), washed in 0.1 M Tris (pH 8.0), centrifuged again, and resuspended in a volume of 0.1 M Tris (pH 8.0) roughly equal to the size of the cell pellet. Each sample was sonicated (XL sonicator, Heat Systems-Ultrasonics, Inc., Farmingdale, N.Y.) with a microtip in 3-mL aliquots on ice for 2 min. each at a 70% cycle with a one-second interval. The lysate was spun in a microcentrifuge at 14,000 g for 10 min. and the supernatant was collected and designated crude cell extract.

The enzyme assays were conducted in a total volume of 1 mL containing 100 mM sodium glycine (pH 9.5), 1 mM 3-hydroxypropionaldehyde (3HPA), 1 mM $NAD^+$ or $NADP^+$, 6 mM dithiothreitol (DTT), and a volume of crude cell extract containing 20-100 µg total protein. A baseline was established prior to adding 3HPA, which started the reaction. The activity given by the DH5α/pFS14 extract was 0.00 U/mg when $NAD^+$ was used and 0.03 U/mg when $NADP^+$ was used. The activity given by the DH5α/pMS33 extract was 1.89 U/mg when $NAD^+$ was used and 0.32 U/mg when $NADP^+$ was used. Thus cells expressing the *E. coli* AldH protein gain the ability to convert 3HPA to 3-hydroxypropionic acid with either $NAD^+$ or $NADP^+$ as cofactor.

Construction of pFS14

The 4hbD gene was cloned by PCR using the plasmid pCK3 (Söhling & Gottschalk, 1996, *J. Bacteriol.* 178:871-80) as a template. The following oligonucleotide primers were used:

```
(4hbD 5' EcoRI)
5'-CTCTGAATTCAAGGAGGAAAAAATATGAAGTTATTAAAATTGGC-3'

(4hbD 3' SacI)
5'-TTTCTCTGAGCTCGGGATATTTAATGATTGTAGG-3'
```

The resulting PCR product was digested with EcoRI and SacI and ligated to plasmid pTrcN that had been digested with the same enzymes. pTrcN is a derivative of pTrc99a (Pharmacia; Uppsala, Sweden); the modification that distinguishes pTrcN is the removal of the NcoI restriction site by digestion with NcoI, treatment with T4 DNA polymerase, and self-ligation.

Construction of pMS33

On the basis of its homology with other aldehyde dehydrogenases, the aldH gene was cloned by PCR from the *E. coli* genome using the following oligonucleotide primers:

```
(aldH 5' Acc65I)
5'-GGTGGTACCTTAAGAGGAGGTTTTTATGAATTTTCATCACCTGGCT
T-3'

(aldH 3' NotI)
5'-GGTGCGGCCGCTCAGGCCTCCAGGCTTATCCA-3'
```

The resulting PCR product was digested with Acc65I and NotI and ligated to pSE380 (Invitrogen; Carlsbad, Calif.) that had been digested with the same enzymes to form pMS33.

Example 2

Growth of *E. coli* with 1,4-Butanediol as Sole Carbon Source

*E. coli* strain LS5218 (obtained from the Yale *E. coli* Genetic Stock Center, New Haven, Conn., as strain CGSC 6966) was transformed with either of two plasmids, pFS76 or pFS77. pFS76 contains the 4HB dehydrogenase (gbd) gene from *Ralstonia eutropha*, as described in Valentin et al. (1995, *Eur. J. Biochem.* 227:43-60). Plasmid pFS77 contains the gbd gene as well as the *E. coli* aldehyde dehydrogenase (aldH) gene and the *Klebsiella pneumoniae* 1,3-propanediol oxidoreductase (dhaT) gene, arranged in a single operon. Both plasmids contain the trc promoter for transcription of the genes.

LS5218/pFS76 and LS5218/pFS77 were streaked onto minimal-medium plates containing 5 g/L of either 4HB (4-hydroxybutyrate, as the sodium salt) or 1,4-butanediol. The plate medium also contained, per liter: 15 g agar; 1 mmol $MgSO_4$; 10 mg thiamine; 25.5 mmol $Na_2HPO_4$; 33.3 mmol $K_2HPO_4$; 27.2 mmol $KH_2PO_4$; 2.78 mg $FeSO_4.7H_2O$; 1.98 mg $MnCl_2.4H_2O$; 2.81 mg $CoSO_4.7H_2O$; 0.17 mg $CuCl_2.2H_2O$; 1.67 mg $CaCl_2.2H_2O$; 0.29 mg $ZnSO_4.7H_2O$; 100 µg ampicillin; and 0.1 mmol IPTG. The plates were incubated overnight at 37° C. Both strains grew on the 4HB plate, but only LS5218/pFS77 grew on the 1,4-butanediol plate. Therefore, it was shown that the pathway consisting of the gbd, aldH, and dhaT genes is sufficient for growth of *E. coli* LS5218 with 1,4-butanediol as the sole carbon source.

Construction of pFS76

The gbd gene was amplified by PCR from the genome of *R. eutropha* H16 (obtained from the American Type Culture Collection, Rockville, Md., as strain ATCC 17699) using the following oligonucleotide primers:

```
(gbd 5' EcoRI)
5'-CCTGAATTCAGGAGGTTTTTATGGCGTTTATCTACTATCTGACCCA
C-3'

(gbd 3' SacI)
5'-CCTGAGCTCCTACCTGCAAGTGCTCGCCGCTC-3'
```

The resulting PCR product was digested with EcoRI and SacI and ligated to pSE380 (Invitrogen; Carlsbad, Calif.) that had been digested with the same enzymes to form pFS76.

Construction of pFS77

The aldH-dhaT region was removed from pMS59 by digestion with NheI and HindIII. Plasmid pFS76 was digested with SpeI and HindIII. NheI and SpeI form compatible sticky ends. The aldH-dhaT fragment from pMS59 and the large fragment of pFS76 were ligated together to give pFS77, containing the gbd, aldH, and dhaT genes, all under control of the trc promoter.

Example 3

Production of Poly(4HB) From 1,4-Butanediol

*Escherichia colt* strain LS5218 (CGSC 6966) was transformed with either of two plasmids, pFS30 or pMS60. pFS30 contains the *Ralstonia eutropha* PRA synthase (phaC) gene and the *Clostridium kluyveri* 4HB-CoA transferase (hbcT) gene, both under control of the trc promoter. pMS60 contains the aldH and dhaT genes along with the two genes in pFS30, all under control of the trc promoter. The objective of the experiment was to determine whether the addition of the aldH and dhaT genes would be beneficial to the conversion of 1,4-butanediol to 4HB in the PHA polymer.

Each strain was grown in LB broth supplemented with 100 g/mL ampicillin overnight at 37° C. with shaking at 250 rpm. The cells were then removed from the medium by centrifugation (2000 g, 10 min.) and resuspended in 100 mL of a medium containing, per liter: 2.5 g LB powder; 50 mmol potassium phosphate, pH 7.0; 2 g glucose; 5 g 1,4-butanediol; 100 µg ampicillin; and 0.1 mmol IPTG. These incubations were at 30° C. with shaking at 250 rpm for 25 hours. The cells from one-quarter of the volume of the flask were centrifuged as above, washed with water, centrifuged again, and lyophilized. About 20 mg of lyophilized cell mass from each flask was subjected to simultaneous extraction and butanolysis at 110° C. for 3 hours in 2 mL of a mixture containing (by volume) 90% 1-butanol and 10% concentrated hydrochloric acid, with 2 mg/mL benzoic acid added as an internal standard. The water-soluble components of the resulting mixture were removed by extraction with 3 mL water. The organic phase (1 µL at a split ratio of 1:50 at an overall flow rate of 2 mL/min) was analyzed on an SPB-1 fused silica capillary GC column (30 m; 0.32 mm ID; 0.25 µm film; Supelco; Bellefonte, Pa.) with the following temperature profile: 80° C., 2 min; 10° C. per min. to 250° C.; 250° C., 2 min. The standard used to test for the presence of 4-hydroxybutyrate units in the polymer was gamma-butyrolactone (Aldrich Chemical Co.; Milwaukee, Wis.).

Strain LS5218/pFS30 reached an optical density (600 nm) of 3.9 and had accumulated poly-4HB to 3.3% of the dry cell weight, while strain LS5218/pMS60 reached an optical density (600 nm) of 6.5 and had accumulated poly-4HB to 12.3% of the dry cell weight. Thus expression of the aldH and dhaT genes is sufficient to increase the ability of *E. coli* LS5218 to synthesize poly-4HB from 1,4-butanediol.

Construction of pFS16

The plasmid pFS16 was constructed by ligating the *Clostridium kluyveri* orfZ (also called hbcT) PCR product to pTrcN. The orfZ gene was amplified by PCR from plasmid pCK3 (Söhling and Gottschalk, 1996, *J. Bacteriol* 178:871-80) using the following oligonucleotide primers:

```
(orfZ 5' AvrII)
5'-TCCCCTAGGATTCAGGAGGTTTTTATGGAGTGGGAAGAGATATATAA
AG-3'

(orfZ 3' SalI)
5'-CCTTAAGTCGACAAATTCTAAAATCTCTTTTTAAATTC-3'
```

The resulting PCR product was digested with AvrII and SalI and ligated to pTrcN that had been digested with XbaI (which is compatible with AvrII) and SalI to form pFS16.

Construction of pFS30

The plasmid pFS30 was derived from pFS16 by adding the *Ralstonia eutropha* PHA synthase (phaC) gene. The plasmid pAeT414 was digested with XmaI and StuI so that the *R. eutropha* promoter and the structural phaC gene were present on one fragment. pFS16 was cut with BamHI, treated with T4 DNA polymerase to create blunt ends, then digested with XmaI. The two DNA fragments thus obtained were ligated together to form pFS30.

Construction of pMS59

The aldH gene was removed from pMS33 by digestion with SpeI and BglII. Plasmid pTC42 (Skraly et al., 1998, *Appl. Environ. Microbiol.* 64:98-105), which contains the *Klebsiella pneumoniae* dhaT gene under the control of the trc promoter, was digested with NheI and BglII. SpeI and NheI form compatible sticky ends. The aldH-containing fragment of pMS33 and the large fragment of pTC42 were ligated together to form pMS59.

Construction of pMS60

The aldH-dhaT region was isolated from pMS59 by digestion with SpeI, followed by treatment with the Klenow fragment of DNA polymerase I and subsequent digestion with MfeI. This fragment had one blunt end and one sticky end compatible with EcoRI-generated sticky ends. pFS30 was digested with XmaI, followed by treatment with the Klenow fragment of DNA polymerase I and subsequent digestion with EcoRI. The large fragment of pFS30 and the aldH-dhaT-containing fragment of pMS59 were ligated together to form pMS60.

Example 4

Synthesis of Poly(3HB-co-4HB) from Glucose and 1,4-Butanediol

*E. coli* strain MBX1493 is a poly(3HB-co-4HB) producing strain with the *C. kluyveri* orfZ; (also called hbcT) gene (Söhling & Gottschalk, 1996, *J. Bacteriol.* 178:871-80) integrated into its chromosome. It was derived from strain MBX1335, a PHB-producing strain with the phaA, phaB, and phaC genes integrated into its chromosome. MBX1335 was itself derived from MBX820 (see PCT WO 00/011188 by Metabolix) by bacteriophage P1 transduction of the phaA, phaB, and phaC genes into strain LS5218.

Strain MBX1493 was transformed with four plasmids in separate procedures: pTrcN, pTC42, pMS33, and pMS59. These plasmids contain, under control of the trc promoter, the following genes, respectively: none, dhaT only, aldH only, both aldH and dhaT. Each of these strains was grown in 3 mL LB supplemented with 100 µg/mL ampicillin at 37° C. with shaking overnight. A volume of 1 mL of each of these cultures was used as an inoculum into 50 mL of a medium containing, per liter: 1 mmol $MgSO_4$; 10 mg thiamine; 25.5 mmol $Na_2HPO_4$; 33.3 mmol $K_2HPO_4$; 27.2 mmol $KH_2PO_4$; 2.78 mg $FeSO_4.7H_2O$; 1.98 mg $MnCl_2.4H_2O$; 2.81 mg $CoSO_4.7H_2O$; 0.17 mg $CuCl_2.2H_2O$; 1.67 mg $CaCl_2.2H_2O$; 0.29 mg $ZnSO_4.7H_2O$; 10 g glucose; 5 g 4-hydroxybutyrate or 10 g 1,4-butanediol; 100 µg ampicillin; 25 µg chloramphenicol; and 0.01 mmol IPTG. These cultures were incubated at 30° C. with shaking at 250 rpm for 88 hours. The cells were removed from this medium by centrifugation (2000 g, 10 min.), and they were lyophilized and analyzed for PHA content and composition by GC. Table 1 shows the composition of the polymers made by these strains and the final optical densities (600 nm) of the cultures.

As shown in Table 1, all strains produce a copolymer with a significant percentage of 4HB when fed 4HB. However, when fed 1,4-butanediol, only the pMS59-containing cells, that is, the cells expressing both aldH and dhaT, achieved a significant level of 4HB incorporation into the polymer. Thus the aldH-dhaT pathway was shown to enable the conversion of 1,4-butanediol to 4HB and not to interfere significantly with cell health or the subsequent incorporation of 4HB into a PHA.

TABLE 1

Conversion of 1,4-butanediol to 4HB

| Substrate | Plasmid | OD (600 nm) | PHA % dcw[a] | 4HB % of polymer[b] |
|---|---|---|---|---|
| 4HB | pTrcN | 19.2 | 53.0 | 36.6 |
| 4HB | pTC42 | 18.8 | 62.7 | 16.0 |
| 4HB | pMS33 | 14.8 | 49.8 | 21.4 |
| 4HB | pMS59 | 22.8 | 43.5 | 32.2 |
| 1,4-BD | pTrcN | 16.0 | 41.0 | 1.1 |
| 1,4-BD | pTC42 | 10.4 | 38.7 | 0.7 |
| 1,4-BD | pMS33 | 10.8 | 40.6 | 2.9 |
| 1,4-BD | pMS59 | 10.4 | 34.6 | 25.3 |

[a]Percent of total dry cell weight.
[b]Percent of total polymer weight.

Example 5

Production of Poly(3HP) from 1,3-Propanediol

*Escherichia coli* strain LS5218 (CGSC 6966) was transformed with either of two plasmids, pFS30 or pMS60. The objective of the experiment was to determine whether the addition of the aldH and dhaT genes would be beneficial to the conversion of 1,3-propanediol to 3HP.

Each strain was grown in LB broth supplemented with 100 µg/mL ampicillin overnight at 37° C. with shaking at 250 rpm. The cells were then removed from the medium by centrifugation (2000 g, 10 min.) and resuspended in 50 mL of a medium containing, per liter: 2.5 g LB powder; 50 mmol potassium phosphate, pH 7.0; 5 g glucose; 0 or 10 g 1,3-propanediol; 100 µg ampicillin; and 0.1 mmol IPTG. These incubations were at 30° C. with shaking at 250 rpm for 25 hours. The cells were removed from the medium by centrifugation as described above, washed with water, centrifuged again, lyophilized, and analyzed for PHA content and composition by GC. The standard used to test for the presence of 3-hydroxypropionate units in the polymer was beta-propiolactone (Aldrich Chemical Co.; Milwaukee, Wis.).

In the flasks without added 1,3-propanediol, no PHP formation was detected; strains LS5218/pFS30 and LS5218/pMS60 reached optical densities (600 nm) of 4.6 and 8.2, respectively. In the flasks with added 1,3-propanediol, strain LS5218/pFS30 reached an optical density (600 nm) of 5.2 and did not accumulate poly-3HP to a detectable level, while strain LS5218/pMS60 reached an optical density (600 nm) of 6.6 and had accumulated poly-3HP to 5.0% of the dry cell weight. Thus expression of the aldH and dhaT genes is sufficient to increase the ability of *E. coli* LS5218 to synthesize poly-3HP from 1,3-propanediol.

Example 6

Synthesis of Poly(3HB-co-3HP) from Glucose and 1,3-Propanediol

Strain MBX1493 was transformed with four plasmids in separate procedures: pTrcN, pTC42, pMS33, and pMS59. Each of these strains was grown in 100 mL LB supplemented with 100 μg/mL ampicillin at 37° C. with shaking overnight. The cells were decanted from each flask, and the residual liquid was retained. To each flask was then added 80 mL of a medium containing, per liter: 6.25 g LB powder; 1 mmol MgSO$_4$; 10 mg thiamine; 25.5 mmol Na$_2$HPO$_4$; 33.3 mmol K$_2$HPO$_4$; 27.2 mmol KH$_2$PO$_4$; 2.78 mg FeSO$_4$.7H$_2$O; 1.98 mg MnCl$_2$.4H$_2$O; 2.81 mg CoSO$_4$.7H$_2$O; 0.17 mg CuCl$_2$.2H$_2$O; 1.67 mg CaCl$_2$.2H$_2$O; 0.29 mg ZnSO$_4$.7H$_2$O; 10 g glucose; 100 μg ampicillin; 25 μg chloramphenicol; and 0.01 mmol IPTG. These cultures were incubated at 37° C. with shaking at 250 rpm for 7 hours. To each flask was then added 20 mL of the same medium given above, except that in this medium LB was increased to 12.5 g/L, glucose was increased to 100 g/L, IPTG was increased to 0.25 mM, and 1,3-propanediol was added at 50 g/L. Thus the final concentrations added at this stage were 2.5 g/L LB, 20 g/L glucose, 10 g/L 1,3-propanediol, and 0.05 mM IPTG. These flasks were incubated at 30° C. for 24 hours with shaking at 250 rpm. The cells were then removed from this medium by centrifugation (2000 g, 10 min.), and they were lyophilized and analyzed for PHA content and composition by GC. Table 2 shows the composition of the polymers made by these strains and the final optical densities (600 nm) of the cultures.

In the absence of 1,3-propanediol, each strain synthesized only PHB. When fed 1,3-propanediol, only the pMS59-containing cells, that is, the cells expressing both aldH and dhaT, achieved a significant level of 3HP incorporation into the polymer. The cells containing pMS33, or aldH alone, do accomplish 3HP incorporation, but to only a small extent. Thus the aldH-dhaT pathway was shown to enable the conversion of 1,3-propanediol to 3HP. The cells containing the dhaT gene (pTC42 and pMS59) made less total polymer when 1,3-propanediol was present, and this is most likely due to the toxicity of 3-hydroxypropionaldehyde. Increasing the ratio of aldH to dhaT expression and/or reducing 1,3-propanediol concentration should subdue this phenomenon.

TABLE 2

Incorporation of 3HP into PHA by MBX1493 Containing Various Plasmids

| 1,3-Propanediol g/L | Plasmid | PHA % dcw[a] | 3HP % of polymer[b] |
|---|---|---|---|
| 0 | pTrcN | 35.2 | 0.0 |
| 0 | pTC42 | 46.0 | 0.0 |
| 0 | pMS33 | 31.2 | 0.0 |
| 0 | pMS59 | 37.7 | 0.0 |
| 10 | pTrcN | 36.6 | 0.0 |
| 10 | pTC42 | 23.9 | 0.0 |
| 10 | pMS33 | 39.6 | 0.3 |
| 10 | pMS59 | 20.0 | 3.8 |

[a]Percent of total dry cell weight.
[b]Percent of total polymer weight.

Example 7

Use of Acyl-CoA Synthetase for Poly(4HB) synthesis from 1,4-Butanediol

Strain MBX1668, which has the aldH and dhaT genes integrated into its chromosome as an operon along with the tetracycline resistance marker from Tn10, was transformed with either of two plasmids: pFS73 or pMS92. The plasmid pFS73 is the same as pFS30 described in previous examples except that the ampicillin resistance marker has been replaced with the kanamycin resistance marker from pACYC177 (GenBank Accession No. X06402). The plasmid pMS92 is derived from pFS73, the orfZ gene having been replaced with the alkK gene from *Pseudomonas oleovorans* (van Beilen et al., 1992, *Mol. Microbiol.* 6:3121-36). Each of these strains was grown in 3 mL LB supplemented with 50 μg/mL kanamycin and 10 μg/mL tetracycline at 37° C. with shaking overnight. One milliliter of each culture was added as an inoculum to a 200-mL square bottle. Each bottle held 50 mL of a medium containing, per liter: 0.1 g casamino acids; 5 mmol MgSO$_4$; 10 mg thiamine; 25.5 mmol Na$_2$HPO$_4$; 33.3 mmol K$_2$HPO$_4$; 27.2 mmol KH$_2$PO$_4$; 2.78 mg FeSO$_4$.7H$_2$O; 1.98 mg MnCl$_2$.4H$_2$O; 2.81 mg CoSO$_4$.7H$_2$O; 0.17 mg CuCl$_2$.2H$_2$O; 1.67 mg CaCl$_2$.2H$_2$O; 0.29 mg ZnSO$_4$.7H$_2$O; 10 g glucose; 10 g 1,4-butanediol; 50 μg kanamycin; and 10 μg tetracycline. These cultures were incubated at 30° C. with shaking at 250 rpm for 48 hours. The cells were then removed from this medium by centrifugation (2000 g, 10 min.), and they were lyophilized and analyzed for PHA content and composition by GC. Strain MBX1668 harboring pFS73 contained 5.8% poly(4HB) by dry weight, while MBX1668 harboring pMS92 contained 27.7% poly(4HB) by dry weight. Thus the alkK gene is an acceptable, and in this case better, substitute for the orfZ gene in the synthesis of PHAs from diols.

Modifications and variations of the methods and materials described herein will be obvious to those skilled in the art and are intended to come within the scope of the following claims.

We claim:

1. Genetically engineered *Escherichia coli* (*E. coli*) for use in producing polyhydroxyalkanoates comprising 4-hydroxybutyrate monomers,
   wherein the *E. coli* expresses enzymes selected from the group consisting of β-ketothiolase, acetoacetyl-CoA reductase and PHA synthase, and at least one enzyme selected from the group consisting of acyl-CoA transferase and acyl-CoA synthetase, and
   wherein the *E. coli* is genetically engineered to express both aldehyde dehydrogenase and diol oxidoreductase, so that when the *E. coli* is provided with 1,4-butanediol and cultured under conditions where the 1,4-butanediol can be converted to 4-hydroxybutyryl-CoA monomer which can then be polymerized to form polyhydroxyalkanoates comprising 4-hydroxybutyrate, the *E. coli* produces polyhydroxyalkanoates comprising 4-hydroxybutyrate monomers.

2. A system for making polyhydroxyalkanoates comprising 4-hydroxybutyrate monomers, the system comprising
   an *E. coli* expressing enzymes selected from the group consisting of β-ketothiolase, acetoacetyl-CoA reductase, and PHA synthase and at least one enzyme selected from the group consisting of acyl-CoA transferase and acyl-CoA synthetase,
   wherein the *E. coli* is genetically engineered to express both aldehyde dehydrogenase and diol oxidoreductase, and
   wherein the *E. coli* can convert 1,4-butanediol into 4-hydroxybutyryl-CoA monomer which can then be polymerized to form polyhydroxyalkanoates comprising 4-hydroxybutyrate.

3. The genetically engineered *E. coli* of claim 1, wherein the 4-hydroxybutyrate monomer is polymerized to form poly-(4-hydroxybutyrate).

4. The genetically engineered *E. coli* of claim 1, wherein the 4-hydroxybutyrate monomer is polymerized to form poly-(3-hydroxybutyrate-co-4-hydroxybutyrate).

5. The system of claim 2, wherein the 4-hydroxybutyrate monomer is polymerized to form poly-(4-hydroxybutyrate).

6. The system of claim 2, wherein the 4-hydroxybutyrate monomer is polymerized to form poly-(3-hydroxybutyrate-co-4-hydroxybutyrate).

7. The genetically engineered *E. coli* of claim 4, wherein 4-hydroxybutyrate incorporation into the poly-(3-hydroxybutyrate-co-4-hydroxybutyrate) polymer by the *E. coli* expressing both aldehyde dehydrogenase and diol oxidoreductase is enhanced when compared to incorporation of 4-hydroxybutyrate into a poly-(3-hydroxybutyrate-co-4-hydroxybutyrate) by *E. coli* expressing only aldehyde dehydrogenase.

8. A method for producing polyhydroxyalkanoates comprising 4-hydroxybutyrate monomers comprising
   providing genetically engineered *Escherichia coli* (*E. coli*) of claim 1,
   providing 1,4-butanediol which can be converted into hydroxyalkanoate monomers by enzymes expressed by the *E. coli*, and
   culturing the *E. coli* under conditions wherein the hydroxyalkanoate monomers are polymerized to form polyhydroxyalkanoates comprising 4-hydroxybutyrate monomers.

9. The method of claim 8 wherein the hydroxyalkanoate monomer is 4-hydroxybutyrate.

* * * * *